(12) United States Patent
Wang et al.

(10) Patent No.: US 7,297,802 B2
(45) Date of Patent: Nov. 20, 2007

(54) PRODUCTION METHODS OF EPOXYTRIAZOLE DERIVATIVE AND INTERMEDIATE THEREFOR

(75) Inventors: Weiqi Wang, Osaka (JP); Tetsuya Ikemoto, Osaka (JP)

(73) Assignee: Sumitomo Chemical Company, Limited, Osaka-shi (JP)

( * ) Notice: Subject to any disclaimer, the term of this patent is extended or adjusted under 35 U.S.C. 154(b) by 551 days.

(21) Appl. No.: 10/842,600

(22) Filed: May 10, 2004

(65) Prior Publication Data

US 2004/0267024 A1 Dec. 30, 2004

Related U.S. Application Data

(62) Division of application No. 10/335,400, filed on Dec. 31, 2002, now Pat. No. 6,884,892.

(30) Foreign Application Priority Data

| Jun. 20, 2002 | (JP) | ............................. 2002/180610 |
| Oct. 28, 2002 | (JP) | ............................. 2002/313317 |
| Oct. 31, 2002 | (JP) | ............................. 2002/318833 |

(51) Int. Cl.
 *C07D 303/00* (2006.01)
(52) U.S. Cl. .................................. 549/419
(58) Field of Classification Search ................. 549/419
 See application file for complete search history.

(56) References Cited

U.S. PATENT DOCUMENTS

| 3,442,912 A | * | 5/1969 | Hatch ........................ 549/519 |
| 5,405,861 A | | 4/1995 | Itoh et al. |

FOREIGN PATENT DOCUMENTS

| EP | 0 061 835 B1 | 10/1982 |
| EP | 0 421 210 A2 | 4/1991 |
| EP | 0 421 600 A1 | 4/1991 |
| EP | 0 657 449 A1 | 6/1995 |
| JP | 04-356471 | 12/1992 |
| JP | 05-230038 | 9/1993 |
| WO | WO 96/25410 A1 | 8/1996 |

OTHER PUBLICATIONS

Gala et al., *Tetrahedron Letters*, 37(5): 611-614 (Jan. 1996).
Gala et al., "Total Chiral Synthesis of Azole Antifungals via α-Hydroxylation of Ketones," *Tetrahedron Letters*, 37 (45), 8117-8120 (1996).
Honda et al., "A General Synthetic Method of Chiral 2-Arylalkanoic Esters via Thermal 1,2-Rearrangement," *Bull. Chem. Soc. Jpn.*, 60 (3), 1027-1036 (1987).
Saji et al., "Stereoselective Synthesis of Antifungal Agent *threo*-2-(2,4-Difluorophenyl)-3-methylsulfonyl-1-(1*H*-1,2,4-triazol-1-yl)-2-butanol (SM-8668)," *Bull. Chem. Soc. Jpn.*, 67 (5), 1427-1433 (1994).
Tasaka et al., "Optically Active Antifungal Azoles. I. Synthesis and Antifungal Activity of (2*R*,3*R*)-2-(2,4-Difluorophenyl)-3-mercapto-1-(1*H*-1,2,4-triazol-1-yl)-2-butanol and Its Stereoisomers," *Chem. Pharm. Bull.*, 41 (6), 1035-1042 (1993).
Tasaka et al., "Optically Active Antifungal Azoles. IV. Synthesis and Antifungal Activity of (2*R*,3*R*)-3-Azolyl-2-(substituted phenyl)-1-(1*H*-1,2,4-triazol-1-yl)-2-butanols," *Chem. Pharm. Bull.*, 43 (3), 432-440 (1995).

* cited by examiner

*Primary Examiner*—Kamal A. Saeed
(74) *Attorney, Agent, or Firm*—Leydig, Voit & Mayer, Ltd.

(57) ABSTRACT

An epoxytriazole derivative (V) useful as an intermediate for anti-fungal agents and an intermediate therefor having high quality can be produced economically and efficiently by the following industrial means. A compound of the following formula (I) is reacted with trimethyloxosulfonium salt and the like in the presence of a base to give compound (II), this compound is converted to compound (IV), and this compound is reacted with 1,2,4-triazole in the presence of a base.

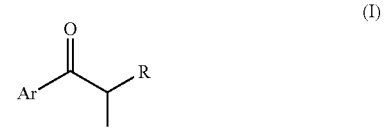

(I)

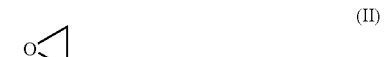

(II)

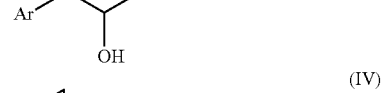

(IV)

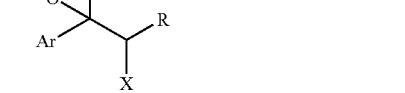

(V)

wherein Ar is a phenyl group optionally substituted by 1 to 3 halogen atom(s) or trifluoromethyl group, R is a hydrogen atom or lower alkyl group, and X is a leaving group.

9 Claims, No Drawings

PRODUCTION METHODS OF EPOXYTRIAZOLE DERIVATIVE AND INTERMEDIATE THEREFOR

CROSS REFERENCE TO RELATED APPLICATIONS

This patent application is a divisional of U.S. patent application No. 10/335,400, filed on Dec. 31, 2002, now U.S. Pat. No. 6,884,892.

TECHNICAL FIELD OF THE INVENTION

The present invention relates to production methods of intermediates, particularly epoxytriazole derivative, for triazole compounds useful as an anti-fungal agent.

BACKGROUND OF THE INVENTION

The epoxytriazole derivative represented by the formula (VI)

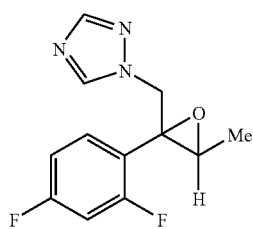

(VI)

(hereinafter to be also referred to as epoxytriazole derivative (VI)) is a useful synthetic intermediate for anti-fungal agents, such as triazole compounds described in JP-A-4-356471, U.S. Pat. No. 5,405,861 and the like.

The production methods of epoxytriazole derivative (VI) have been reported in, for example, Bulletin of the Chemical Society of Japan (Bull. Chem. Soc. Jpn), Vol. 67, 1427-1433 (1994), The Chemical Society of Japan, May 1994, vol. 67, No. 5, pp. 1427-1433, Chemical & Pharmaceutical Bulletin (Chem. Pharm. Bull.), Vol. 43(3), 432-440 (1995), Pharmaceutical Society of Japan, vol. 43, No. 3, pp. 432-440 (1995) and the like. According to these methods, as shown in the following reaction schemes, epoxidation of a compound of the formula (VII) (hereinafter to be also referred to as compound (VII)) wherein hydroxyl group is protected by a protecting group, such as tetrahydropyranyl group and the like, is conducted using trimethyloxosulfonium halide.

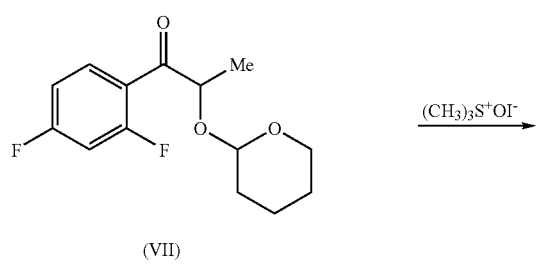

(VII)

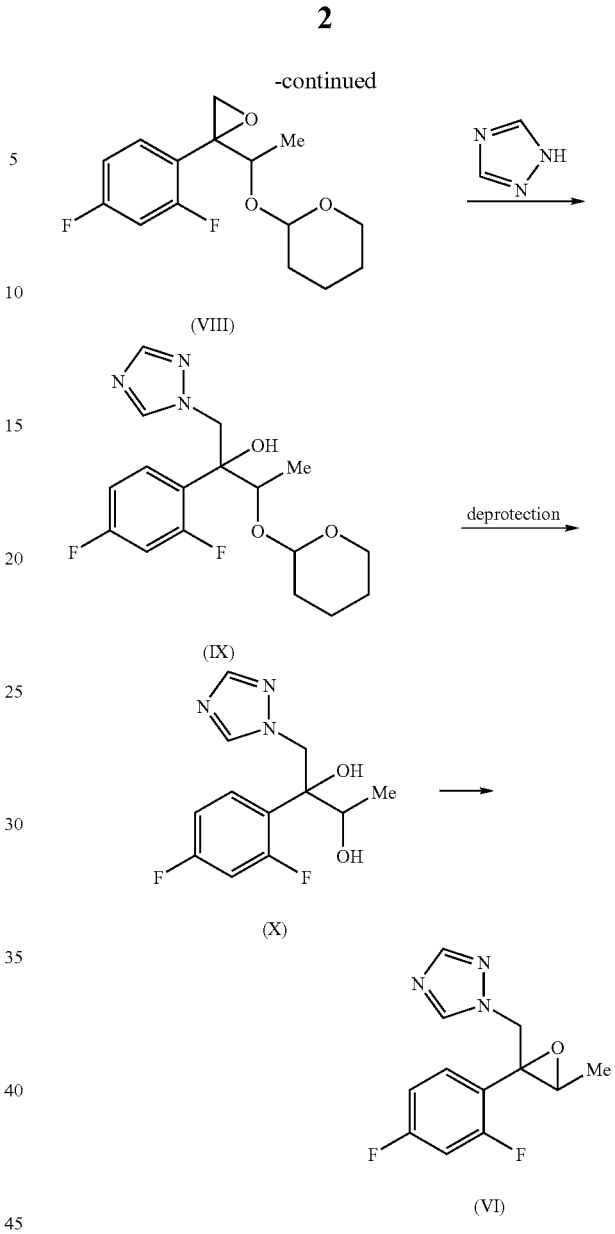

The compound (VII) used as a starting material in conventional methods can be produced by protecting hydroxyl group of a compound, wherein tetrahydropyranyl group of the formula (VII) has been substituted by hydroxyl group (to be also referred to as a deprotected compound of compound (VII)), with tetrahydropyranyl group. However, the introduction of a protecting group is uneconomical because it requires an equimolar amount of tetrahydropyranyl derivative relative to the deprotected compound of compound (VII), and the like. In addition, the introduction of protecting group necessitates a deprotection step, thus increasing the number of steps and the like. Moreover, the introduction of protecting group leads to inefficiency. Thus, this method is industrially disadvantageous. According to conventional methods, moreover, stereoisomers, which are in a diastereomeric relationship and resist use thereof as an intermediate for a triazole compound, which is an anti-fungal agent, are by-produced in about 20%. The α-hydroxy-ketone derivative, which is a deprotected compound of compound (VII), is chemically unstable, and the above-mentioned epoxidation without protection of hydroxyl group has been considered to be difficult.

It is therefore an object of the present invention to provide a method for economically and efficiently producing epoxytriazole derivative (V) to be mentioned below, such as epoxytriazole derivative (VI) and the like, or an intermediate therefor, with high quality by an industrial means.

SUMMARY OF THE INVENTION

As a result of the intensive studies done by the present inventors, they have found that the above-mentioned epoxidation unexpectedly proceeds even without protecting the deprotected compound of compound (VII), which has been expected to be difficult. Furthermore, they have found that diastereoselectivity can be dramatically improved, which resulted in the completion of the present invention. Accordingly, the present invention provides the following.

1. A production method of a compound of the formula (II)

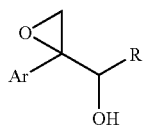

(II)

wherein

Ar is a phenyl group optionally substituted by 1 to 3 halogen atom(s) or a trifluoromethyl group, and R is a hydrogen atom or a lower alkyl group, (hereinafter to be also referred to as compound (II)), which comprises reacting a compound of the formula (I)

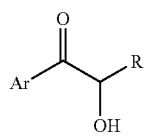

(I)

wherein each symbol is as defined above (hereinafter to be also referred to as compound (I)) with a trimethyloxosulfonium salt or a trimethylsulfonium salt in the presence of a base.

2. The production method of the aforementioned 1, wherein Ar is a 2,4-difluorophenyl group and R is a methyl group.

3. A production method of a compound of the formula (III)

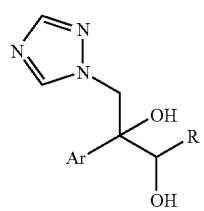

(III)

wherein each symbol is as defined above (hereinafter to be also referred to as compound (III)), or a salt thereof, which comprises reacting compound (I) with a trimethyloxosulfonium-salt or a trimethylsulfonium salt in the presence of a base to give compound (II).

4. The production method of the aforementioned 3, further comprising reacting the compound (II) with 1,2,4-triazole in the presence of a base.

5. The production method of the aforementioned 3 or 4, wherein Ar is a 2,4-difluorophenyl group and R is a methyl group.

6. A production method of a compound of the formula (IV)

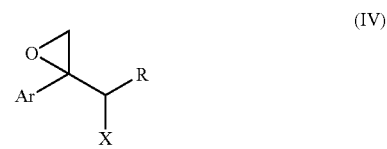

(IV)

wherein X is a leaving group, and other symbols are as defined above (hereinafter to be also referred to as compound (IV)), which compises reacting compound (I) with a trimethyloxosulfonium salt or a trimethylsulfonium salt in the presence of a base to give compound (II).

7. The production method of the aforementioned 6, which further comprises converting compound (II) to compound (IV).

8. The production method of the aforementioned 6 or 7, wherein Ar is a 2,4-difluorophenyl group and R is a methyl group.

9. A production method of an epoxytriazole derivative of the formula (V)

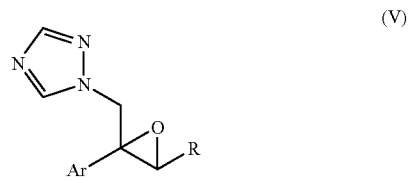

(V)

wherein each symbol is as defined above, (hereinafter to be also referred to as epoxytriazole derivative (V)), or a salt thereof, which comprises reacting compound (I) with a trimethyloxosulfonium salt or a trimethylsulfonium salt in the presence of a base to give compound (II).

10. The production method of the aforementioned 9, which further comprises converting compound (II) to compound (IV) and then reacting the compound (IV) with 1,2,4-triazole in the presence of a base.

11. The production method of the aforementioned 9 or 10, wherein Ar is a 2,4-difluorophenyl group and R is a methyl group.

12. The production method of any of the aforementioned 2, 5, 8 and 11, wherein the compound of the formula (I) is (2R)-2',4'-difluoro-2-hydroxypropiophenone obtained by deprotection of (2R)-2-(1-ethoxyethoxy)-1-(2,4-difluorophenyl)-1-propanone.

13. (2R)-2-(1-Ethoxyethoxy)-1-(2,4-difluorophenyl)-1-propanone.

DETAILED DESCRIPTION OF THE INVENTION

The present invention is explained in detail in the following.

The definition of each symbol is explained below.

The alkyl in the present invention is linear when it does not have a prefix (e.g., iso, neo, sec-, tert- and the like). When simply put, for example, "propyl" means linear propyl.

The "halogen atom" of "phenyl group optionally substituted by 1 to 3 halogen atom(s) or a trifluoromethyl group" is exemplified by fluorine atom, chlorine atom, bromine atom, iodine atom and the like, with preference given to fluorine atom.

The "phenyl group optionally substituted by 1 to 3 halogen atom(s) or a trifluoromethyl group" is exemplified by phenyl group, 2-fluorophenyl group, 3-fluorophenyl group, 4-fluorophenyl group, 2-chlorophenyl group, 3-chlorophenyl group, 4-chlorophenyl group, 4-bromophenyl group, 4-iodophenyl group, 2,3-difluorophenyl group, 2,4-difluorophenyl group, 3,4-difluorophenyl group, 3,5-difluorophenyl group, 2,6-difluorophenyl group, 2,3-dichlorophenyl group, 2,4-dichlorophenyl group, 3,4-dichlorophenyl group, 3,5-dichlorophenyl group, 2,6-dichlorophenyl group, 2,4-dibromophenyl group, 2,4,6-trifluorophenyl group, 2-trifluoromethylphenyl group, 3-trifluoromethylphenyl group, 4-trifluoromethylphenyl group and the like, with preference given to 2,4-difluorophenyl group.

The "lower alkyl group" means linear or branched chain alkyl group preferably having 1 to 12, more preferably 1 to 3, carbon atoms. Examples thereof include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl and the like, with preference given to methyl.

The "trimethyloxosulfonium salt" is exemplified by trimethyloxosulfonium chloride, trimethyloxosulfonium bromide, trimethyloxosulfonium iodide, trimethyloxosulfonium methylsulfate and the like. In view of easy availability, trimethyloxosulfonium bromide and trimethyloxosulfonium iodide are preferable.

Examples of "trimethylsulfonium salt" include trimethylsulfonium chloride, trimethylsulfonium bromide, trimethylsulfonium iodide, trimethylsulfonium methylsulfate and the like. In view of easy availability, trimethylsulfonium bromide and trimethylsulfonium iodide are preferable.

The "leaving substituent" and "leaving group" are the same, and, for example, $-OSO_2R^1$ ($R^1$ is optionally substituted lower alkyl group or optionally substituted phenyl group) and the like are mentioned, with preference given to $-OSO_2CH_3$.

The "lower alkyl group" of the above-mentioned "optionally substituted lower alkyl group" for $R^1$ is as defined for the aforementioned "lower alkyl group".

The substituent for the above-mentioned "optionally substituted lower alkyl group" for $R^1$ is exemplified by halogen atom such as fluorine atom, chlorine atom, bromine atom, iodine atom and the like, and the like, with preference given to fluorine atom.

Examples of the above-mentioned "optionally substituted lower alkyl group" for $R^1$ include methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl, fluoromethyl, trifluoromethyl and the like, with preference given to methyl and trifluoromethyl.

The substituent of the above-mentioned "optionally substituted phenyl group" for $R^1$ is exemplified by lower alkyl group, halogen atom and the like, wherein "lower alkyl group" and "halogen atom" are as defined for the aforementioned "lower alkyl group" and "halogen atom", and is preferably methyl.

The above-mentioned "optionally substituted phenyl group" for $R^1$ is exemplified by phenyl group, 2-methylphenyl group, 3-methylphenyl group, 4-methylphenyl group, 4-ethylphenyl group, 4-propylphenyl group, 4-isopropylphenyl group, 2-chlorophenyl group, 3-chlorophenyl group, 4-chlorophenyl group, 4-fluorophenyl group, 4-bromophenyl group and the like, with preference given to 4-methylphenyl group.

In compound (I)—compound (IV) and epoxytriazole derivative (V) of the present invention, Ar is particularly preferably 2,4-difluorophenyl group and R is particularly preferably methyl group.

The compound (I)—compound (IV) and epoxytriazole derivative (V) of the present invention may have one or more asymmetric carbon atoms, and compound (I)—compound (IV) and epoxytriazole derivative (V) of the present invention encompass all the imaginable optically active forms and mixtures thereof (e.g., racemates, enantiomer mixtures, diastereomer mixtures and the like). The preferable configurational compounds (I)—(IV) are respectively compounds of the formulae:

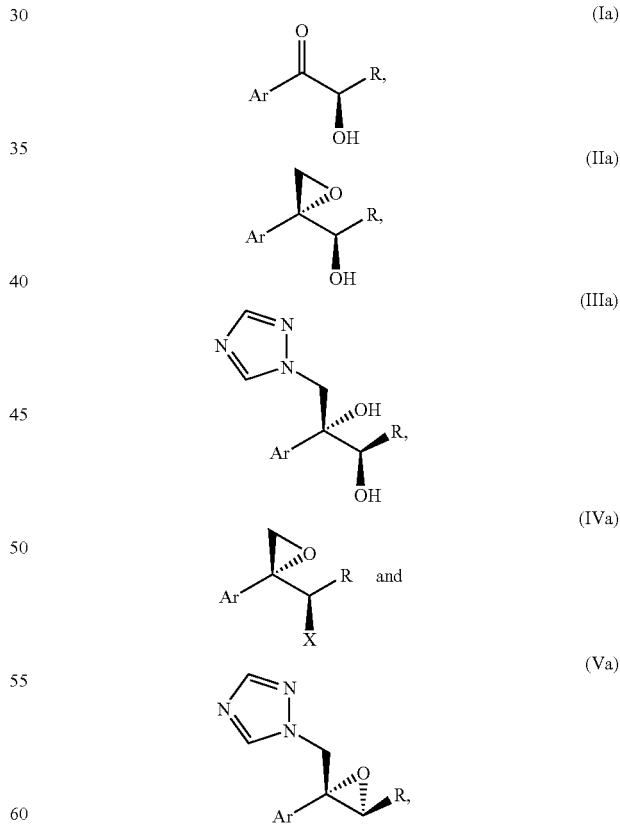

wherein each symbol is as defined for the aforementioned 1 and 6.

The compound (III) and epoxytriazole derivative (V) have a 1,2,4-triazole ring, and may take the form of a salt. The salts of compound (III) and epoxytriazole derivative (V)

include, for example, salts with mineral acids (e.g., hydrochloric acid, sulfuric acid, nitric acid, phosphoric acid and the like), organic acids (e.g., acetic acid, propionic acid, methanesulfonic acid, 4-toluenesulfonic acid and the like), and the like.

The production methods of the present invention are shown in the following schemes in summary fashion.

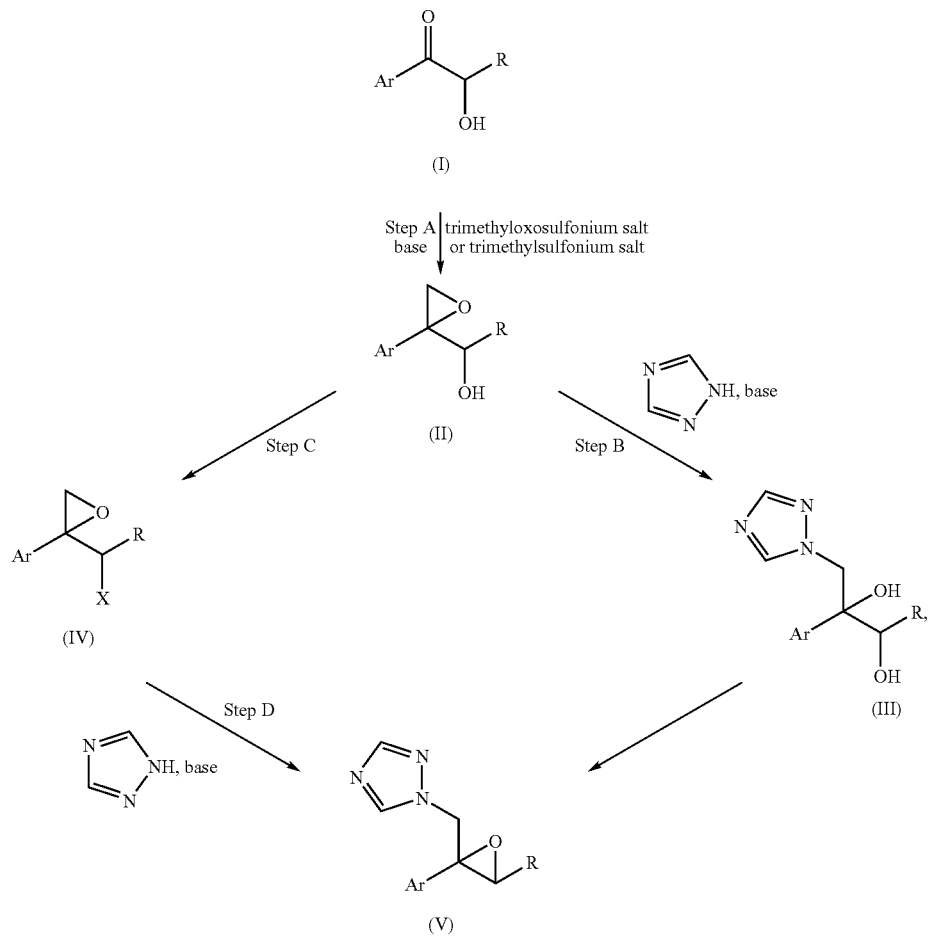

wherein each symbol is as defined for the aforementioned 1 and 6.

1. Production Method of Compound (II) (Step A)

The compound (II) can be obtained by, for example, reacting compound (I) with trimethyloxosulfonium salt or trimethylsulfonium salt in a solvent in the presence of a base. The order of addition of the reagents is not particularly limited, and, for example, trimethyloxosulfonium salt or trimethylsulfonium salt and a base may be added to a solvent and then compound (I) may be added; or a solution of trimethyloxosulfonium salt or trimethylsulfonium salt may be added to a solvent and then a base may be added thereto to allow reaction and the obtained solution may be added to a solution of compound (I) in a solvent.

The base to be used in Step A is not particularly limited as long as it reacts with trimethyloxosulfonium salt or trimethylsulfonium salt to give sulfur ylide. Examples thereof include alkali metal hydroxides such as potassium hydroxide, sodium hydroxide, lithium hydroxide and the like; alkali metal hydrides such as sodium hydride, potassium hydride, lithium hydride and the like; alkyl-alkali metals such as n-butyllithium, methyllithium, n-hexyllithium and the like; alkali metal amides such as sodium amide, potassium amide, lithium diisopropyl amide, lithium dicyclohexyl amide, lithium hexamethyl disilazide and the like; alkali metal alkoxides such as potassium tert-butoxide, sodium tert-butoxide, sodium methoxide, sodium ethoxide, potassium methoxide, potassium ethoxide and the like; and the like, with preference given to sodium hydride. Sodium hydride may be dispersed in mineral oil such as liquid paraffin and the like and added dropwise.

The amount of the base to be used in Step A is generally 0.25 mol-1.1 mol, preferably 0.5 mol-1.0 mol, more preferably 0.6 mol-0.9 mol, relative to 1 mol of trimethyloxosulfonium salt or trimethylsulfonium salt. When the amount of the base to be used in Step A is less than 0.25 mol relative to 1 mol of trimethyloxosulfonium salt or trimethylsulfonium salt, trimethyloxosulfonium salt or trimethylsulfonium salt remains more than necessary, which is economically disadvantageous, and unpreferably causes side reaction. When the amount of the base to be used exceeds 1.1 mol relative to 1 mol of trimethyloxosulfonium salt or trimethylsulfonium salt, a base unreacted with trimethyloxosulfonium salt or trimethylsulfonium salt remains in excess, which is economically disadvantageous and causes a side reaction (mostly isomerization) to possibly degrade the yield and quality.

The amount of trimethyloxosulfonium salt or trimethylsulfonium salt to be used in Step A is generally 0.8 mol-5.0 mol, preferably 1.0 mol-3.0 mol, more preferably 1.1 mol-2.5 mol, relative to 1 mol of compound (I). When the amount of trimethyloxosulfonium salt or trimethylsulfonium salt to be used in Step A is less than 0.8 mol relative to 1 mol of compound (I), compound (I) partly remains unreacted to possibly lower the yield. When the amount of trimethyloxosulfonium salt or trimethylsulfonium salt to be used exceeds 5.0 mol relative to 1 mol of compound (I), the effect corresponding to the amount used cannot be afforded, which is economically disadvantageous.

The solvent to be used in Step A may be any as long as it does not inhibit the reaction. Examples thereof include ethers such as tetrahydrofuran (THF), methyl tert-butyl ether, 1,4-dioxane, diethylene glycol dimethyl ether (diglyme), ethylene glycol dimethyl ether, 1,3-dioxolane, 2-methyltetrahydrofuran and the like; aprotic polar solvents such as N,N-dimethylformamide (DMF), N,N-dimethylacetamide (DMAc), dimethyl sulfoxide (DMSO), sulfolane, N-methyl-2-pyrrolidinone (NMP), 1,3-dimethyl-2-imidazolidinone (DMI), hexamethyl phosphoramide (HMPA), nitrobenzene, carbon disulfide, acetonitrile, propionitrile and the like; halogenated solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, monofluorobenzene and the like; aromatic hydrocarbon such as toluene, xylene and the like; and the like, and a mixed solvent thereof. When a mixed solvent is used, the solvents may be mixed at optional ratios by a conventionally known method.

The amount of the solvent to be used is generally 1 L-50 L, preferably 4 L-30 L, more preferably 5 L-25 L, relative to 1 kg of compound (I).

While the reaction temperature in Step A depends on the reagent to be used and the like, the reaction of Step A generally proceeds from −40° C. to 120° C., preferably from −20° C. to 60° C., more preferably from −10° C. to 40° C., generally for 0.5 hr-24 hr, preferably 1 hr-8 hr.

The compound (II) to be obtained in Step A can be isolated and purified by a conventional method. For example, the reaction mixture is poured into water and partitioned, the organic layer is washed and filtrated, and the obtained filtrate is washed, dried and concentrated under reduced pressure to isolate compound (II). After the isolation, for example, it is subjected to silica gel column chromatography for purification. The compound (II) can be used for the next reaction without purification.

The compound (I), which is a starting material in Step A, is a known compound and can be synthesized by a method described in Bull. Chem. Soc. Jpn, Vol. 60, 1027-1036 (1987) and the like. For example, compound (I) wherein Ar is a 2,4-difluorophenyl group and R is methyl, can be obtained by deprotection of the tetrahydropyranyloxy group of compound (VII) disclosed in Bull. Chem. Soc. Jpn, Vol. 67, 1427-1433 (1994), by a known method. An optically active compound (I) can be obtained by deprotection of optically active compound (VII) disclosed in Chem. Pharm. Bull., Vol. 41(6), 1035-1042 (1993) in the same manner, or by the method described in Tetrahedron Letters, 37, 8117-8120 (1996). By the use of optically active compound (I), an optically active form of compound (II) can be obtained.

(2R)-2-1,4'-Difluoro-2-hydroxypropiophenone, which is one of compounds (I), can be produced by deprotection of (2R)-2-(1-ethoxyethoxy)-1-(2,4-difluorophenyl)-1-propanone. (2R)-2-(1-Ethoxyethoxy)-1-(2,4-difluorophenyl)-1-propanone is a novel compound, and can be produced by a method described in Reference Example 1 below or a method analogous thereto. That is, (R)-alkyl lactate is reacted with dialkylamine to give (R)-dialkyl lactamide, which is reacted with ethyl vinyl ether to protect hydroxyl group with 1-ethoxyethyl group, and then reacted with 2,4-difluorophenylmagnesium halide.

2. Production Method of Compound (III) (Step B)

The compound (III) can be obtained by, for example, reacting compound (II) with 1,2,4-triazole in a solvent in the presence of a base. The order of addition of the reagents is not particularly limited. For example, 1,2,4-triazole and a base may be added to a solvent and then compound (II) may be added; or 1,2,4-triazole may be added to a solvent and a base may be added to allow reaction and the solution may be added to a solution of compound (II) in a solvent.

The base to be used in Step B is not particularly limited as long as it forms a stable salt with 1,2,4-triazole. Examples thereof include alkali metal hydroxides such as sodium hydroxide, potassium hydroxide, lithium hydroxide and the like; alkali metal carbonates such as potassium carbonate, sodium carbonate, lithium carbonate, cesium carbonate and the like; alkali metal hydrides such as sodium hydride, potassium hydride, lithium hydride and the like; alkyl-alkali metals such as n-butyllithium, methyllithium, n-hexyllithium and the like; alkali metal amides such as sodium amide, potassium amide, lithium diisopropyl amide, lithium dicyclohexyl amide, lithium hexamethyl disilazide and the like; alkali metal alkoxides such as potassium tert-butoxide, sodium tert-butoxide, potassium methoxide, sodium methoxide, sodium ethoxide, potassium ethoxide and the like; tertiary amines such as 1,8-diazabicyclo[5.4.0]-7-undecene, 1,5-diazabicyclo[4.3.0]-5-nonene, 1,4-diazabicyclo[2.2.2]octane, N,N,N',N'-tetramethylethylene diamine, N,N-diisopropylethylamine, triethylamine and the like; and the like, with preference given to sodium hydride and potassium carbonate. Sodium hydride may be dispersed in mineral oil such as liquid paraffin and the like and added dropwise.

The amount of the base to be used in Step B is generally 0.3 mol-1.3 mol, preferably 0.5 mol-1.1 mol, more preferably 0.8 mol-1.0 mol, relative to 1 mol of 1,2,4-triazole. The amount of the base to be used in Step B, which is less than 0.3 mol relative to 1 mol of 1,2,4-triazole, is unpreferable, because 1,2,4-triazole remains more than necessary, which is economically disadvantageous, and 1,2,4-triazole remaining after the reaction needs to be separated. When the amount of the base to be used exceeds 1.3 mol relative to 1 mol of 1,2,4-triazole, a base that does not react with 1,2,4-triazole remains in excess, which is economically disadvantageous, and causes a side reaction to possibly degrade the yield and quality.

The amount of 1,2,4-triazole to be used in Step B is generally 0.8 mol-5.0 mol, preferably 1.0 mol-3.0 mol, more preferably 1.1 mol-2.0 mol, relative to 1 mol of compound (II). When the amount of 1,2,4-triazole to be used in Step B is less than 0.8 mol relative to 1 mol of compound (II), compound (II) partly remains unreacted to possibly lower the yield. The amount of 1,2,4-triazole to be used, which exceeds 5.0 mol relative to 1 mol of compound (II), is unpreferable, because 1,2,4-triazole not involved in the reaction remains in excess, which is economically disadvantageous, and 1,2,4-triazole remaining after reaction needs to be separated.

To promote the reaction in Step B, for example, a phase-transfer catalyst such as tetraalkyl ammonium salts (e.g., octadecyl trimethyl ammonium bromide, tetrabutyl ammonium sulfate, tetrabutyl ammonium bromide, tetrabutyl ammonium iodide, tetrabutyl ammonium chloride and the like), trialkyl benzyl ammonium salts (e.g., benzyl trimethyl ammonium bromide, benzyl trimethyl ammonium chloride, benzyl triethyl ammonium chloride and the like); and the like may be added.

The solvent to be used in Step B may be any as long as it does not inhibit the reaction. Examples thereof include ethers such as THF, methyl tert-butyl ether, 1,4-dioxane, diethylene glycol dimethyl ether (diglyme), ethylene glycol dimethyl ether, 1,3-dioxolane, 2-methyltetrahydrofuran and the like; aprotic polar solvents such as DMF, DMAc, DMSO, sulfolane, NMP, DMI, HMPA, methyl isobutyl ketone, methyl ethyl ketone, acetone, cyclohexanone, 3-pentanone, nitrobenzene, carbon disulfide, acetonitrile, propionitrile and the like; halogenated solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, monofluorobenzene and the like; aromatic hydrocarbon such as toluene, xylene and the like; and the like, and a mixed solvent thereof. When a mixed solvent is used, the solvents may-be mixed at optional ratios by a conventionally known method.

The amount of the solvent to be used is generally 1 L-50 L, preferably 3 L-30 L, more preferably 5 L-25 L, relative to 1 kg of compound (II).

While the reaction temperature in Step B depends on the reagent to be used and the like, the reaction of Step B generally proceeds from −20° C. to 150° C., preferably from 0° C. to 100° C., more preferably from 20° C. to 90° C., generally for 0.5 hr-24 hr, preferably 1 hr-10 hr.

The compound (III) to be obtained in Step B can be isolated and purified by a conventional method. For example, the reaction mixture is poured into water and partitioned, the organic layer is washed and filtrated, and the obtained filtrate is washed, dried and concentrated under reduced pressure to isolate compound (III). After the isolation, for example, it is subjected to silica gel column chromatography for purification. The compound (III) can be used for the next reaction without purification.

The epoxytriazole derivative (V) can be derived from compound (III) by a known method, for example, a method described in Bull. Chem. Soc. Jpn, Vol. 67, 1427-1433 (1994).

3. Production Method of Compound (IV) (Step C)

The compound (IV) can be produced by, for example, introducing hydroxyl group of compound (II) into sulfonic acid ester (—OSO$_2$R$^1$).

In Step C, a method for deriving hydroxyl group of compound (II) into sulfonic acid ester may be, for example, a method comprising reacting compound (II) with sulfonyl halide of the formula: YSO$_2$R$^1$ (XI) wherein Y is chlorine atom or bromine atom and R$^1$ is as defined above (hereinafter to be also referred to as sulfonyl halide (XI)), or sulfonic anhydride of the formula: —O(SO$_2$R$^1$)$_2$ (XII) wherein R$^1$ is as defined above (hereinafter to be also referred to as sulfonic anhydride (XII)) in a solvent in the presence of a base. The order of addition of the reagents is not particularly limited. For example, compound (II) and base may be added to a solvent and then sulfonyl halide (XI) or sulfonic anhydride (XII) (hereinafter to be also referred to as sulfonyl halide and the like, when these are not particularly distinguished) may be added; or compound (II), sulfonyl halide and the like may be added to a solvent and then a base may be added.

The base to be used in Step C is, for example, aliphatic tertiary amines (e.g., trimethylamine, triethylamine, tributylamine, diisopropylethylamine, N-methylmorpholine and the like), aromatic amines (e.g., pyridine, picoline, 2,6-lutidine, collidine, 4-(N,N-dimethylamino)pyridine, N,N-dimethylaniline, N,N-diethylaniline and the like) or alkali metal carbonates (e.g., sodium carbonate, potassium carbonate and the like), basic ion-exchange resins (e.g., amberlight IRA-67, amberlight IRA-900 and the like), and the like. Preferred is triethylamine or sodium carbonate, and particularly preferred is triethylamine.

The amount of the base to be used in Step C is generally 0.8 mol-3.0 mol, preferably 1.0 mol-2.0 mol, more preferably 1.0 mol-1.5 mol, relative to 1 mol of sulfonyl halide and the like. When the amount of the base to be used in Step C is less than 0.8 mol relative to 1 mol of sulfonyl halide and the like, the generated acid cannot be trapped and side reaction occurs. In addition, the reaction rate tends to be unpreferably late. When the amount of the base to be used exceeds 3.0 mol relative to 1 mol of sulfonyl halide and the like, the effect corresponding to the amount used cannot be afforded, which is economically disadvantageous.

The amount of sulfonyl halide and the like to be used in Step C is generally 0.8 mol-3.0 mol, preferably 1.0 mol-2.0 mol, more preferably 1.0 mol-1.5 mol, relative to 1 mol of compound (II). When the amount of sulfonyl halide and the like to be used in Step C is less than 0.8 mol relative to 1 mol of compound (II), compound (II) partly remains unreacted to possibly lower the yield. When the amount of sulfonyl halide and the like to be used exceeds 3.0 mol relative to 1 mol of compound (II), sulfonyl halide and the like not involved in the reaction remains in excess, which is economically disadvantageous, and unpreferably causes side reaction.

The solvent to be used in Step C may be any as long as it does not inhibit the reaction. Examples thereof include methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, monofluorobenzene, nitrobenzene, carbon disulfide, toluene, acetonitrile, propionitrile, methyl tert-butyl ether, ethylene glycol dimethyl ether, diethylene glycol dimethyl ether, tetrahydrofuran, 2-methyltetrahydrofuran, 1,3-dioxolane, 1,4-dioxane and the like, with preference given to toluene. In addition, a mixed solvent thereof may be used, and when a mixed solvent is used, the solvents may be mixed at optional ratios by a conventionally known method.

The amount of the solvent to be used is generally 1 L-50 L, preferably 4 L-30 L, more preferably 5 L-25 L, relative to 1 kg of compound (II).

While the reaction temperature in Step C depends on the reagent to be used and the like, the reaction of Step C generally proceeds from −30° C. to 80° C., preferably from −10° C. to 60° C., more preferably from −5° C. to 30° C., generally for 0.5 hr-24 hr, preferably 1 hr-10 hr.

The compound (IV) to be obtained in Step C can be isolated and purified by a conventional method. For example, the reaction mixture is poured into water and partitioned, the organic layer is washed and filtrated, and the obtained filtrate is washed, dried and concentrated under reduced pressure to isolate compound (IV). After the isolation, for example, it is subjected to silica gel column chromatography for purification. The compound (IV) can be used for the next reaction without purification.

The compound (II), which is a starting material in Step B and Step C, is a known compound and, for example, that obtained in the above-mentioned Step A can be used. By the use of optically active compound (I) as the starting material of the above-mentioned Step A, an optically active compound (II) can be obtained. In Step B or Step C, the use of an optically active compound (II) affords an optically active compound (III) or an optically active compound (IV).

4. Production Method of Epoxytriazole Derivative (V) (Step D)

The epoxytriazole derivative (V) can be obtained by, for example, reacting compound (IV) with 1,2,4-triazole in a solvent in the presence of a base. The order of addition of the reagents is not particularly limited. For example, 1,2,4-triazole and a base may be added to a solvent and then compound (IV) may be added; or 1,2,4-triazole may be added to a solvent, a base may be added to allow reaction and the obtained solution may be added to a solution of compound (IV) in a solvent.

The base to be used in Step D is not particularly limited as long as it forms a stable salt with 1,2,4-triazole. Examples thereof include alkali metal hydroxides such as sodium hydroxide, potassium hydroxide, lithium hydroxide and the like; alkali metal carbonates such as potassium carbonate, sodium carbonate, lithium carbonate, cesium carbonate and the like; alkali metal hydrides such as sodium hydride, potassium hydride, lithium hydride and the like; alkyl-alkali metals such as n-butyllithium, methyllithium, n-hexyllithium and the like; alkali metal amides such as sodium amide, potassium amide, lithium diisopropyl amide, lithium dicyclohexyl amide, lithium hexamethyl disilazide and the like; alkali metal alkoxides such as potassium tert-butoxide, sodium tert-butoxide, potassium methoxide, sodium methoxide, sodium ethoxide, potassium ethoxide and the like; and the like, with preference given to sodium hydride, potassium carbonate and sodium methoxide. Sodium hydride may be dispersed in mineral oil such as liquid paraffin and the like and added dropwise.

The amount of the base to be used in Step D is generally 0.3 mol-1.3 mol, preferably 0.5 mol-1.1 mol, more preferably 0.8 mol-1.0 mol, relative to 1 mol of 1,2,4-triazole. The amount of the base to be used in Step D, which is less than 0.3 mol relative to 1 mol of 1,2,4-triazole, is unpreferable, because 1,2,4-triazole remains more than necessary, which is economically disadvantageous, and 1,2,4-triazole remaining after reaction needs to be separated. When the amount of the base to be used in Step D exceeds 1.3 mol relative to 1 mol of 1,2,4-triazole, a base that does not react with 1,2,4-triazole remains in excess, which is economically disadvantageous, and causes a side reaction to possibly degrade the yield and quality.

The amount of 1,2,4-triazole to be used in Step D is generally 0.8 mol-5.0 mol, preferably 1.0 mol-3.0 mol, more preferably 1.1 mol-2.0 mol, relative to 1 mol of compound (IV). When the amount of 1,2,4-triazole to be used in Step D is less than 0.8 mol relative to 1 mol of compound. (IV), compound (IV) partly remains unreacted to possibly lower the yield. The amount of 1,2,4-triazole to be used, which exceeds 5.0 mol relative to 1 mol of compound (IV), is unpreferable, because 1,2,4-triazole not involved in the reaction remains in excess, which is economically disadvantageous, and 1,2,4-triazole remaining after reaction needs to be separated.

To promote the reaction in Step D, for example, a phase-transfer catalyst such as tetraalkyl ammonium salts (e.g., octadecyl trimethyl ammonium bromide, tetrabutyl ammonium sulfate, tetrabutyl ammonium bromide, tetrabutyl ammonium iodide, tetrabutyl ammonium chloride and the like), trialkyl benzyl ammonium salts (e.g., benzyl trimethyl ammonium bromide, benzyl trimethyl ammonium chloride, benzyl triethyl ammonium chloride and the like); and the like may be added.

The solvent to be used in Step D may be any as long as it does not inhibit the reaction. Examples thereof include ethers such as THF, methyl tert-butyl ether, 1,4-dioxane, diethylene glycol dimethyl ether (diglyme), ethylene glycol dimethyl ether, 1,3-dioxolane, 2-methyltetrahydrofuran and the like; aprotic polar solvents such as DMF, DMAC, DMSO, sulfolane, NMP, DMI, HMPA, methyl isobutyl ketone, methyl ethyl ketone, acetone, cyclohexanone, 3-pentanone, nitrobenzene, carbon disulfide, acetonitrile, propionitrile and the like; halogenated solvents such as methylene chloride, 1,2-dichloroethane, monochlorobenzene, 1,2-dichlorobenzene, 2-chlorotoluene, 3-chlorotoluene, 4-chlorotoluene, 2-chloro-m-xylene, 2-chloro-p-xylene, 4-chloro-o-xylene, 2,3-dichlorotoluene, 2,4-dichlorotoluene, 2,5-dichlorotoluene, 2,6-dichlorotoluene, 3,4-dichlorotoluene, monofluorobenzene and the like; aromatic hydrocarbon such as toluene, xylene and the like; and the like, or a mixed solvent thereof may be used. When a mixed solvent is used, the solvents may be mixed at optional ratios by a conventionally known method.

The amount of the solvent to be used is generally 1 L-50 L, preferably 3 L-30 L, more preferably 5 L-25 L, relative to 1 kg of compound (IV).

While the reaction temperature in Step D depends on the reagent to be used and the like, the reaction of Step D generally proceeds from −20° C. to 150° C., preferably 0° C.-100° C., more preferably 20° C.-90° C., generally for 0.5 hr-24 hr, preferably 1 hr-10 hr.

The epoxytriazole derivative (V) to be obtained in Step D can be isolated and purified by a conventional method. For example, the reaction mixture is poured into water and partitioned, the organic layer is washed and filtrated, and the obtained filtrate is washed, dried and concentrated under reduced pressure to isolate epoxytriazole derivative (V). After the isolation, for example, it can be subjected to silica gel column chromatography and recrystallization for purification. The epoxytriazole derivative (V) can be also used for the reaction to lead to the objective pharmaceutical product compound without purification.

The compound (IV), which is a starting material in Step D, is a known compound and, for example, that obtained in the above-mentioned Step C can be used. By the use of optically active compound (II) as the starting material of the above-mentioned Step C, an optically active compound (IV) can be obtained. In Step D, the use of an optically active compound (IV) affords an optically active epoxytriazole derivative (V).

The epoxytriazole derivative (V) can be led to a triazole compound useful as an anti-fungal agent, according to a method described in, for example, JP-A-4-356471, JP-A-5-230038 and the like.

The present invention is described in more detail in the following by means of Examples and Reference Examples, which are not to be construed as limitative.

REFERENCE EXAMPLE 1

(2R)-2',4'-difluoro-2-hydroxypropiophenone.

N,N-Dimethylamine (405.7 g, 9.0 mol) was blown in a solution of (D)-methyl lactate (469 g, 4.5 mol) in methanol (234 mL) at 0-15° C. and the solution was stirred in a sealed vessel at 60-65° C. for 24 hr. The reaction mixture was concentrated under reduced pressure to give (D)-N,N-dimethyl lactamide (525 g). To the solution of a part (109 g, 0.93 mol) of the obtained (D)-N,N-dimethyl lactamide in THF (97 mL) were successively added dropwise methanesulfonic acid (0.9 g, 9.4 mmol) and ethyl vinyl ether (74 g, 1.03 mol) at 15-20° C. and the mixture was stirred for 5 hr to give a solution of (2R)-N,N-dimethyl-2-O-(1-ethoxyethyl) lactamide in THF. Subsequently, to this amide solution was dropwise added a solution of 2,4-difluorophenylmagnesium bromide, which had been synthesized from 2,4-difluorobromobenzene (180 g, 0.93 mol) and magnesium (23 g, 0.95 mol) by a conventional method, in THF (485 mL) at room temperature. The mixture was stirred overnight. The reaction solution was flown into cooled aqueous ammonium chloride solution, neutralized with aqueous citric acid solution and extracted 3 times with toluene. The organic layer was mixed and the mixture was washed successively with aqueous ammonium chloride solution and water to give a solution of (2R)-2-(1-ethoxyethoxy)-1-(2,4-difluorophenyl)-1-propanone in toluene. Subsequently, methanol (97 mL) and methanesulfonic acid (0.9 g, 9.4 mmol) were added, and the mixture was stirred at 40° C. for 2.5 hr. The reaction mixture was washed successively with 5% brine (once) and water (two times) and the organic layer was concentrated under reduced pressure to give the title compound as a pale-yellow oil (120 g, yield 69%). (2R)-N,N-dimethyl-2-O-(1-ethoxyethyl) lactamide:

$^1$H-NMR(CDCl$_3$, δ ppm) 1.15-1.41(9H,m), 2.95(s), 2.96 (s), 3.10(s), 3.13(s)(total 6H,N(CH$_3$)$_2$), 3.47-3.70(2H,m, OCH$_2$C), 4.50(q,J=7 Hz), 4.62(q,J=7 Hz)(total 1H,H-2), 4.68(q,J=5 Hz), 4.78(q,J=5 Hz)(total 1H,OCHC).

(2R)-2-(1-ethoxyethoxy)-1-(2,4-difluorophenyl)-1-propanone:

$^1$H-NMR(CDCl$_3$, δ ppm) 1.09(t,J=7 Hz), 1.16(t,J=7 Hz) (total 3H,OCCH$_3$), 1.30(d,J=5 Hz), 1.37(d,J=5 Hz)(total 3H,OCCH$_3$), 1.41(d,J=7 Hz), 1.44(d,J=7 Hz)(total 3H,H-3), 3.45-3.60(2H,m,OCH$_2$C), 4.74-4.85(1H,m,OCHC), 4.89(q, J=7 Hz), 5.05(q,J=7 Hz)(total 1H,H-2), 6.85-6.91(1H,m), 6.95-7.00(1H,m), 7.89-7.98(1H,m).

REFERENCE EXAMPLE 2

(2R)-2',4'-difluoro-2-hydroxypropiophenone (2R)-2',4'-Difluoro-2-(3,4,5,6-tetrahydro-2H-pyran-2-yloxy)propiophenone (9.62 g, 35.6 mmol, synthesized according to the description in Chem. Pharm. Bull., Vol. 41(6), 1035-1042 (1993)) was dissolved in ethanol (99.5%, 50 mL), and pyridinium p-toluenesulfonate (0.89 g, 3.6 mmol) was added. The mixture was stirred at 50-60° C. for 1 hr. After cooling, the reaction mixture was concentrated under reduced pressure to about 10 mL. Water (20 mL) was flown in and the mixture was extracted twice with ethyl acetate (50 mL). The layers extracted with ethyl acetate were mixed, washed with saturated brine (20 mL) and dried over anhydrous magnesium sulfate. After filtration, the filtrate (ethyl acetate solution) was concentrated. The obtained concentrate (about 9.5 g) was subjected to silica gel column chromatography (SiO$_2$, 30 g) and eluted with n-heptane-ethyl acetate (10:1→5:1). The objective fraction was concentrated to give the title compound as a pale-yellow oil (6.00 g, yield: 91%).

EXAMPLE 1

(2R,3R)-3-(2',4'-difluorophenyl)-3,4-epoxy-2-butanol

Trimethyloxosulfonium bromide (2.66 g, 15.4 mmol) was dissolved in dimethyl sulfoxide (13 mL), and sodium hydride (60% dispersion in oil, 0.27 g, 6.79 mmol) was added by small portions at room temperature. After generation of hydrogen stopped, a solution (5 mL) of (2R)-2',4'-difluoro-2-hydroxypropiophenone (1.10 g, 5.91 mmol) in dimethyl sulfoxide was slowly added dropwise, and the mixture was stirred for about 30 min. After completion of the reaction, the reaction mixture was added dropwise to water (50 mL) and extracted twice with ethyl acetate (50 mL). The layers extracted with ethyl acetate were mixed, washed twice with water (20 mL) and dried over anhydrous magnesium sulfate. After filtration, the filtrate (ethyl acetate solution) was concentrated. The obtained concentrate was subjected to silica gel column chromatography (SiO$_2$, 10 g) and eluted with n-heptane—ethyl acetate (10:1→2:1). The objective fraction was concentrated to give a colorless oil (1.06 g). The obtained colorless oil was analyzed by high performance liquid chromatography (HPLC) for area percentage. As a result, it was a 12:1 mixture of mainly the title compound and a diastereomer thereof, (2R,3S)-compound.

HPLC Analysis Conditions column: Symmetry C18 (manufactured by Waters, 5 μm, 3.9 mm×150 mm), column temperature: 35° C., mobile phase: 20% CH$_3$CN—H$_2$O (v/v), detection wavelength: 254 nm, retention time: (2R,3S)-compound; 13.9 min, (2R,3R)-compound; 14.3 min.

$^1$H-NMR (CDCl$_3$, δ ppm) (2R,3R)-compound: 1.16(3H, d,J=7 Hz), 1.79(1H,d,J=8 Hz), 2.80(1H,d,J=5 Hz), 3.30(1H, d,J=5 Hz), 4.07-4.11(1H,m), 6.78-7.91(2H,m), 7.38-7.44 (1H,m). (2R,3S)-compound: 1.19(3H,d,J=6 Hz), 2.22(1H, br.s), 2.91(1H,d,J=5 Hz), 3.28(1H,d,J=5 Hz), 4.07-4.11(1H, m), 6.78-7.91(2H,m), 7.38-7.44(1H,m).

EXAMPLE 2

(2S,3S)-3-(2',4'-difluorophenyl)-3,4-epoxy-2-butanol

Trimethyloxosulfonium iodide (3.56 g, 16.2 mmol) was dissolved in a mixed solvent of dimethyl sulfoxide (16 mL) and tetrahydrofuran (10 mL), and the mixture was cooled to 0-5° C. Sodium hydride (60% dispersion in oil, 0.5 g, 12.4 mmol) was added by small portions at 0-5° C. After generation of hydrogen stopped, the mixture was aged for 4 hr. A solution (6 mL) of (2S)-21,4'-difluoro-2-hydroxypropiophenone (2.0 g, 10.08 mmol) in dimethyl sulfoxide was added dropwise at 0-5° C. over 5 hr. After confirmation of the completion of the reaction by HPLC analysis, the reaction mixture added dropwise to water (52 mL) and the mixture was extracted twice with ethyl acetate (26 ml). The layers extracted with ethyl acetate were mixed, washed twice with brine (10 mL) and dried over anhydrous magnesium sulfate. After filtration, the filtrate (ethyl acetate solution) was concentrated to give a pale-yellow oil (2.03 g). The obtained pale-yellow oil was analyzed under the above-mentioned HPLC conditions for area percentage. As a result, it was a 25:1 mixture of mainly the title compound and a diastereomer thereof, (2S,3R)-compound.

The $^1$H-NMR data were the same as those obtained in Example 1.

EXAMPLE 3

(2S,3S)-2-(2,4-difluorophenyl)-1-(1H-1,2,4-triazol-1-yl)-2,3-butanediol

Trimethyloxosulfonium iodide (17.7 g, 80.6 mmol) was dissolved in a mixed solvent of dimethyl sulfoxide (80 ml) and tetrahydrofuran (30 ml) and the mixture was cooled to 0-5° C. Sodium hydride (60% dispersion in oil, 2.47 g, 61.9 mmol) was added by small portions at 0-5° C. After generation of hydrogen stopped, the mixture was aged for 1.5 hr, and a solution (20 ml) of (2S)-2',4'-difluoro-2-hydroxypropiophenone (10.0 g, 53.8 mmol) in dimethyl sulfoxide was added dropwise at −5 to 5° C. over 3.5 hr. After confirmation of the completion of the reaction by HPLC analysis, 1,2,4-triazole (12.8 g, 185.7 mmol) and potassium carbonate (14.8 g, 107.6 mmol) were added and the mixture was heated at an internal temperature of 90-93° C. for 2 hr. After confirmation of the completion of the addition reaction by HPLC analysis, water (200 ml) was flown in and the mixture was extracted 3 times with ethyl acetate (100 ml). The layers extracted with ethyl acetate were mixed, washed twice with water (100 ml) and dried over anhydrous magnesium sulfate. After filtration, the filtrate (ethyl acetate solution) was concentrated. The obtained oil (13.5 g) was washed successively with a mixed solvent of ethyl acetate (10 ml) and n-heptane (30 ml) and then with a mixed solvent of ethyl acetate (5 ml) and n-heptane (10 ml), after which dispersion crystallized from methyl tert-butyl ether (20 ml). Filtration and drying gave the title compound as white crystals (2.25 g). The filtrate was concentrated, and the obtained concentrate (8.03 g) was subjected to HPLC quantitative determination analysis. As a result, 4.76 g of the title compound was contained. The total yield was 48.5%. The HPLC analysis conditions were the same as in Example 1 (retention time: 7.5 min).

$^1$H-NMR(CDCl$_3$, bppm) 0.98(3H,d,J=6 Hz), 2.62(1H,d, J=9 Hz), 4.31-4.34(1H,m), 4.79, 4.80(each 1H,d,J=14 Hz), 4.82(1H,s), 6.72-6.79(2H,m), 7.38-7.45(1H,m), 7.83,7.85 (each 1H,s).

EXAMPLE 4

(2S,3R)-2-(2,4-difluorophenyl)-3-methyl-2-[(1H-1,2,4-triazol-1-yl)methyl]oxilane A mixture (12:1, 0.3 g, 1.5 mmol) of (2R,3R)-3-(2',4'-difluorophenyl)-3,4-epoxy-2-butanol and a diastereomer thereof ((2R,3S)-compound), which was obtained in Example 1, and triethylamine (0.312 mL, 2.25 mmol) were added to toluene (5 mL) and the mixture was cooled to 0-10° C. Methanesulfonyl chloride (0.14 mL, 1.8 mmol) was added dropwise, and the mixture was stirred for 1 hr. After confirmation of the completion of the reaction by reversed phase HPLC, water (20 mL) and ethyl acetate (50 mL) were added for partitioning. The obtained ethyl acetate layer was washed with saturated brine (20 mL) and dried over anhydrous magnesium sulfate. After filtration, the filtrate (ethyl acetate solution) was concentrated to give (2R,3R)-3-(2',4'-difluorophenyl)-3,4-epoxy-2-methanesulfonyloxybutane as an oil (about 0.42 g).

To a solution (3 mL) of 1,2,4-triazole (0.259 g, 3.75 mmol) in N,N-dimethylformamide was added small portions of sodium hydride (60% dispersion in oil, 0.12 g, 3.0 mmol) at about 20° C., and the mixture was stirred for about 3 hr until hydrogen was not generated. To a solution of sodium salt of 1,2,4-triazole thus obtained was added dropwise a solution (5.5 mL) of the total amount of (2R,3R)-3-(21,4'-difluorophenyl)-3,4-epoxy-2-methanesulfonyoxybutane obtained above in N,N-dimethylformamide at room temperature. The mixture was stirred at 75-80° C. for 1.5 hr. The reaction mixture was added dropwise to water (20 mL), and the mixture was extracted 3 times with ethyl acetate (20 mL). The extracted ethyl acetate layers were mixed, and the mixture was washed twice with saturated brine (10 mL) and dried over anhydrous magnesium sulfate. After filtration, the filtrate (ethyl acetate solution) was concentrated and the obtained concentrate was subjected to silica gel column chromatography (SiO$_2$, 5 g) and eluted with n-heptane—ethyl acetate (10:1)→ethyl acetate. The objective fraction was concentrated to give a pale-yellow oil (0.297 g). The obtained pale-yellow oil was crystallized from a mixed solvent of ethyl acetate (1 mL)—n-heptane (4 mL) to give the title compound (0.185 g, yield from (2R)-2',4'-difluoro-2-hydroxypropiophenone: 44%). As a result of analysis by HPLC, the optical purity was 100% e.e.

HPLC Analysis Conditions column: Chiralcel OD-H (manufactured by DAICEL CHEMICAL, 4.6 mm×250 mm), column temperature: 30° C., mobile phase: 10% isopropanol—n-hexane (v/v), detection wavelength: 254 nm, retention time: (2R,3S)-compound; 14.7 min, (2S,3R)-compound; 19.1 min.

$^1$H-NMR (CDCl$_3$, δ ppm) 1.64(3H,d,J=6 Hz), 3.19(1H, q,J=6 Hz), 4.43, 4.88(each 1H,d,J=15 Hz), 6.70-6.80(2H,m), 6.90-7.04(1H,m), 7.81, 7.96(each 1H,s).

COMPARATIVE EXAMPLE 1

(2R,3R)-3-(2',4'-difluorophenyl)-3,4-epoxy-2-butyl-[3,4,5,6-tetrahydro-2H-pyran-2-yl]ether Sodium hydride (60% dispersion in oil, 0.68 g, 17.0 mmol) was added to dimethyl sulfoxide (40 mL) and trimethyloxosulfonium iodide (3.91 g, 17.8 mmol) was added in small portions at 15-20° C. After generation of hydrogen stopped, a solution (8 mL) of (2R)-2',4'-difluoro-2-(3,4,5,6-tetrahydro-2H-pyran-2-yloxy)propiophenone (4.0 g, 14.8 mmol) in dimethyl sulfoxide was added dropwise, and the mixture was stirred at room temperature for 1 hr. After the completion of the reaction, the reaction mixture was added dropwise to water (120 mL), and the mixture was extracted 3 times with ethyl acetate (120 mL, 80 mL×2). The layers extracted with ethyl acetate were mixed, washed twice with saturated brine (40 mL) and dried over anhydrous magnesium sulfate. After filtration, the filtrate (ethyl acetate solution) was concentrated. The obtained concentrate was subjected to silica gel column chromatography (SiO$_2$, 50 g) and eluted with n-heptane—ethyl acetate (10:1). The objective fraction was concentrated and a mixture of mostly the title compound and a diastereomer thereof, (2R, 3S)-compound, as a pale-yellow oil (3.84 g).

The protecting group of the obtained pale-yellow oil was removed by the same method as in Reference Example 1 and analyzed under the same HPLC conditions as in Example 1. As a result, the ratio of the title compound and a diastereomer thereof, (2R,3S)-compound, was 4:1.

As shown by the above results, the reaction of the compound (I) not protected with trimethyloxosulfonium salt and the like surprisingly proceeded easily to give compound (II). When compound (I) was in an optically active form, induction of racemization in this reaction was worried, but racemization was not observed in most cases. As shown in Comparative Example 1 and Examples 1 and 2, the use of compound (I) resulted in strikingly improved diastereoselectivity as compared to the use of a compound protected by tetrahydropyranyl group. As shown in Example 4, moreover, epoxytriazole derivative (V) could be synthesized efficiently from compound (IV), which was produced by substituting the hydroxyl group in compound (II) for a leaving group.

According to the production method of the present invention, the steps of protection and deprotection can be eliminated and diastereoselectivity can be strikingly improved. Moreover, by substituting the hydroxyl group for a leaving group in compound (II), epoxytriazole derivative (V) and an intermediate therefor having high quality can be produced economically and efficiently by an industrial means.

This application is based on patent application Nos. 2002-180610, 2002-313317 and 2002-318833 filed in Japan, the contents of which are hereby incorporated by reference.

What is claimed is:

1. A production method of a compound of the formula (II)

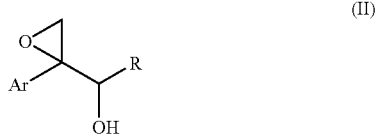

(II)

wherein
Ar is a phenyl group optionally substituted by 1 to 3 halogen atom(s) or a trifluoromethyl group, and
R is a hydrogen atom or a lower alkyl group,
which comprises reacting a compound of the formula (I)

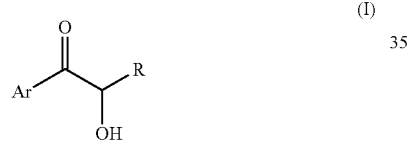

(I)

wherein each symbol is as defined above, with a trimethyloxosulfonium salt or a trimethylsulfonium salt in the presence of a base, wherein the hydroxyl group of the compound of formula (I) is not protected prior to reaction with the trimethyloxosulfonium salt or trimethylsulfonium salt.

2. The production method of claim 1, wherein Ar is a 2,4-difluorophenyl group and R is a methyl group.

3. A production method of a compound of the formula (IV)

(IV)

wherein
Ar is a phenyl group optionally substituted by 1 to 3 halogen atom(s) or a trifluoromethyl group,
R is a hydrogen atom or a lower alkyl group, and
X is a leaving group,
which comprises reacting a compound of the formula (I)

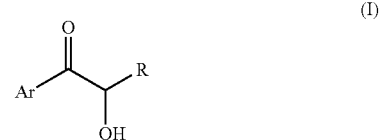

(I)

wherein each symbol is as defined above, with a trimethyloxosulfonium salt or a trimethylsulfonium salt in the presence of a base to give a compound of the formula (II)

(II)

wherein each symbol is as defined above, and wherein the hydroxyl group of the compound of formula (I) is not protected prior to reaction with the trimethyloxosulfonium salt or trimethylsulfonium salt.

4. The production method of claim 3, which further comprises converting the compound of the formula (II) to a compound of the formula (IV)

(IV)

wherein each symbol is as defined in claim 3.

5. The production method of claim 3, wherein Ar is a 2,4-difluorophenyl group and R is a methyl group.

6. The production method of claim 2, wherein the compound of the formula (I) is (2R)-2',4'-difluoro-2-hydroxypropiophenone obtained by deprotection of (2R)-2-(1-ethoxyethoxy)-1-(2,4-difluorophenyl)-1-propanone.

7. The production method of claim 4, wherein Ar is a 2,4-difluorophenyl group and R is a methyl group.

8. The production method of claim 5, wherein the compound of the formula (I) is (2R)-2',4'-difluoro-2-hydroxypropiophenone obtained by deprotection of (2R)-2-(1-ethoxyethoxy)-1-(2,4-difluorophenyl)-1-propanone.

9. The production method of claim 7, wherein the compound of the formula (I) is (2R)-2',4'-difluoro-2-hydroxypropiophenone obtained by deprotection of (2R)-2-(1-ethoxyethoxy)-1-(2,4-difluorophenyl)-1-propanone.

* * * * *